United States Patent [19]
Beckers et al.

[11] Patent Number: 5,837,462
[45] Date of Patent: Nov. 17, 1998

[54] TUMORIGENIC CELL LINES ALTERED BY GENETIC ENGINEERING AND THEIR USE FOR THE TESTING OF ANTITUMOR DRUGS

[75] Inventors: Thomas Beckers, Frankfurt; Thomas Klenner, Ingelheim; Silke Baasner, Hanau, all of Germany

[73] Assignee: Asta Medica Aktiengesellschaft, Germany

[21] Appl. No.: 746,383

[22] Filed: Nov. 8, 1996

[30] Foreign Application Priority Data

Nov. 10, 1995 [DE] Germany .................. 195 42 051.9

[51] Int. Cl.$^6$ ...................................... C12Q 1/68
[52] U.S. Cl. ............................ 435/6; 435/357; 435/320.1
[58] Field of Search ............................ 435/6, 320.1, 357, 435/371, 366, 353

[56] References Cited

PUBLICATIONS

Ghattas et al., *Mol. Cell. Biol.,* v.11, 1991, pp. 5848–5859.
Dirks et al, *Gene,* vol. 128, 1993, pp.247–249.

*Primary Examiner*—James Ketter
*Attorney, Agent, or Firm*—Cushman Darby & Cushman IP Group of Pillsbury Madison & Sutro LLP

[57] ABSTRACT

The invention describes a novel method for determining the mass of vital tumor cells of xenotransplants in animal models. Cells altered by genetic engineering which form a tumor after transplantation synthesize an excreted reporter gene. This is shown by way of example for a secreted form of human placenta-specific, alkaline phosphate (SEAP). The latter can be demonstrated in the serum of test animals or in culture supernatants. The activity of SEAP in the serum correlates with the number of vital tumor cells in the animal and can be measured prior to the formation of a palpable tumor. The invention shows the use of cell lines altered by genetic engineering in such a manner in subcutaneous and orthotopic tumor models. Dicistronic, eukaryotic expression vectors are used for the stable transfection of the mammalian cell lines or tumor cells used. These vectors contain, under the control of a constitutive or inducible promotor element, the gene coding for SEAP, coupled with a second gene. This latter gene codes e.g. for a receptor tyrosine kinase such as erbB2/HER2 which transforms during overexpression.

7 Claims, 9 Drawing Sheets

FIG. 3E 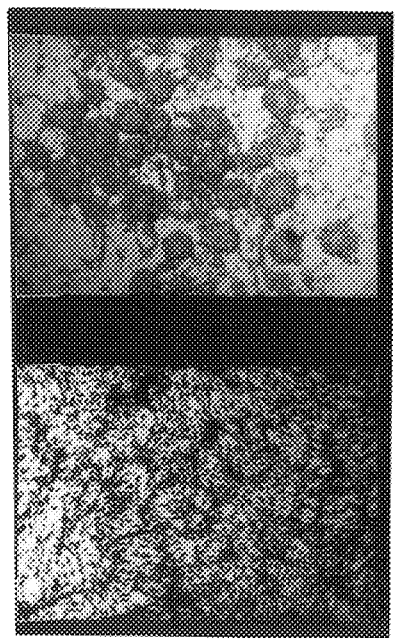 FIG. 3F 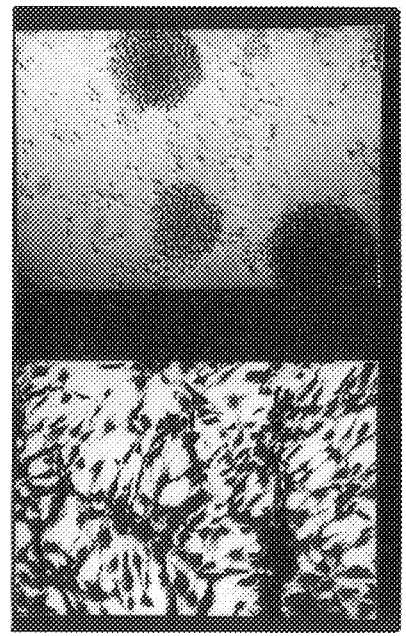
FIG. 3G FIG. 3H

TUMORIGENIC CELL LINES ALTERED BY GENETIC ENGINEERING AND THEIR USE FOR THE TESTING OF ANTITUMOR DRUGS

This application is based on application no. 19542051.9 filed in Germany on Nov. 10, 1995, the content of which is incorporated hereinto by reference.

BACKGROUND OF THE INVENTION

1. Field of the Invention

The invention relates to vectors whose sequence contains a gene coding for a reporter protein, to tumorigenic cell lines altered by genetic engineering with the vectors and to the use of the latter cell lines for the testing of antitumor drugs.

2. Background Information

Reporter genes code for simple proteins and proteins which can be demonstrated in very small amounts, which proteins usually have an enzymatic activity. They are used in genetic engineering with preference in functional testing systems for examining regulatory genetic elements (Rosenthal, Meth. Enzym. 152, 704–720, 1987) but have also proven to be superb for other applications, especially for testing systems for high-throughput screening systems in the pharmaceutical industry. The classic reporter gene is chloramphenicol acetyl transferase (CAT; Gorman et al., Mol. Cell. Biol. 2, 1044–1051, 1982). However, it has been very largely replaced by other reporter genes. The following are to be named here: β-galactosidase (An et al., Mol. Cell. Biol. 2, 1628–1632, 1982), *Photinus pyralis luciferase* (Dew et et al., Mol. Cell. Biol. 7, 725–737, 1987) and "green fluorescent protein" (GFP; Chalfie et al., Science 263, 802–805, 1994). These reporter proteins have the fact in common that they are expressed intracellularly. On the other hand, a secreted expression is advantageous for many applications. The human, placenta-specific, alkaline phosphatase (SEAP; Berger et al., Gene 66, 1–10, 1988) and a secreted luciferase from *Vargula hilgendorfii* (Thompson et al., Proc. Natl. Acad. Sci. U.S.A. 86, 6567–6571, 1989, Thompson et al., Gene 96, 257–262, 1990) have been described in the literature as secreted reporter proteins. In principle, however, an intracellularly expressed reporter protein can also be expressed in a secreted manner by alteration by genetic engineering. This becomes possible if appropriate signals, e.g. in the form of a eukaryotic signal sequence, are introduced by genetic engineering into the cDNA gene.

Alkaline phosphatases (APs; E.C. 3.1.3.1) are ubiquitous enzymes present in very varied isoforms. Four distinct genetic loci are present in man which code for the tissue-nonspecific AP as well as the tissue-specific forms from the placenta (PLAP), from the intestinal tract (IAP) and from germ cells (GCAP) (Millán, Anticancer Res. 8, 995–1004, 1988). Malignant diseases are frequently associated with a change of the AP isoenzyme profile. Thus, an unphysiologically high activity of PLAP in the serum and cancerous tissue was demonstrated by Fishman et al. in 1968 in patients with lung cancer (Fishman et al., Cancer Res. 28, 150–154, 1968). PLAP has also been described as tumor marker in testicular cancer (Lange et al., Cancer Res. 42, 3244–3247, 1982) as well as in benign and malignant neoplasias of the ovary (Nouwen et al., Cancer Res. 45, 892–902, 1985). However, there is no causal connection between the malignant degeneration and the expression of alkaline phosphate, especially PLAP. This was shown by enzymatic histochemical stainings for heat-stable AP in normal and malignant cervical tissue (Nozawa et al., in Alkaline Phosphatases, 223–234, Alan R. Liss Inc., New York, 1984) as well as in experiments with human cell hybrids (Stanbridge et al., Proc. Natl. Acad. Sci. U.S.A. 79, 6242–6245, 1982).

The cDNA coding for PLAP was cloned (Millán, J. Biol. Chem. 261, 3112–3115, 1986), and codes for an enzyme expressed in a membrane-based manner probably via a phosphatidyl inositol glycane link. It is distinguished from the other APs by a pronounced thermal stability and an inability to be inhibited by the inhibitor homoarginine. This also makes possible a logical utilization of PLAP for experiments in genetic engineering, especially its use in modified form as reporter gene. J. Berger was the first to describe a form of PLAP which was shortened by genetic engineering, is expressed by cells in excreted form. This was designated as SEAP (Berger et al., Gene 66, 1–10, 1988; EP 0,327,960 A1). A heat-stable phosphatase constituting a heterodimer of PLAP and IAP is excreted from the KB cell line, which was established from a human carcinoma of the buccal mucous membrane (Luduena & Sussman, J. Biol. Chem. 251, 2620–2628, 1976; Kodama et al., Biochem. Biophys. Acta 1218, 163–1172, 1994). The placenta-specific, alkaline phosphatase excreted by genetic-engineering modification (SEAP) has been used as reporter gene especially for studies on the eukaryotic expression of genes (Cullen & Malim, Meth. Enzym. 216, 362–268, 1992; Jones et al., Oncogene 6, 745–751, 1991).

The examination of substances for anti-proliferative activity takes place using in vitro and in vivo testing systems. A broad testing in an initial screening in vitro usually takes place on established tumor cell lines or on model cell lines which become tumorigenic by transfection with a transforming gene. A plurality of established tumor cell lines are available for the in vitro testing (Alley et al., Cancer Res. 48, 589–601, 1988), in which a cellular parameter such as, for example, the metabolic activity or the DNA synthesis is quantified, usually using a simple test. A simple test which determines the cellular dehydrogenase activity is available in the form of the XTT assay (Scudiero et al., Cancer Res. 48, 4827–4833, 1988). Alternatively, cell-free, recombinant testing systems are becoming increasingly significant for the discovering of target-specific tumor drugs, especially in high-throughput screening. Note in this connection the use of recombinantly produced receptor proteins or signal coupling proteins in ELISA tests for finding receptor antagonists. Even if the number of guide structures can be limited by a well-thought-out screening hierarchy, the testing in a valid tumor model in vivo, for example a xenotransplant on a nude mouse, is an essential component of preclinical testing.

The in vivo testing on solid tumors often takes place for xenotransplants of human tumors in a nude mouse or a scid (severe combined immune deficiency) mouse. Both instances concern immunodeficient mouse breeds which tolerate the transplanted tumor cells. The classic testing of antitumor drugs in nude mice takes place by subcutaneous implantation of human tumor tissue or injection of cells of a tumor cell line established in vitro. A subcutaneous tumor of very differing morphology and growth properties forms which is very dependent on the implanted cellular material (cell number, vitality and tumorigenicity). This tumor can also result in the formation of metastases in the animal, depending on its aggressiveness and invasiveness. The growth of the subcutaneous tumor and therewith the rate of proliferation of the tumor cells forming it is simply measured with a sliding caliper or quantified by palpitation and comparison with a plasticine model (Druckrey et al., Drug Res. 6, 539–550, 1956). The tumor size is indicated by the tumor volume (cm$^3$) or the tumor mass (g). In the treatment of a test animal the inhibition of the tumor growth or the regression of the tumor is designated as a curative action of a substance. Likewise, the extension of life is a measure of the healing effect of an active substance. This is relevant in particular in the case of tumors which do not grow subcutaneously. Various disadvantages are apparent in this procedure which were not able to be avoided previously in the technical execution of the testing. If, for example, a solid, subcutaneous tumor becomes necrotic as a consequence of a treatment in the inner cell layers, this may not be detectable by palpitation. If a subcutaneously transplanted tumor metastasizes into various organs, these metastases are hidden at first and only become visible as a result of the adverse impact on the functioning of the affected organ or after a biopsy.

SUMMARY OF THE INVENTION

Accordingly, it is an object of the present invention to provide an animal model which makes it possible to quantify the total number of vital tumor cells in the entire organism under the influence of a therapy without palpitation or biopsy. In particular, the invention has the goal of realizing this animal model by means of altering cell lines with suitable vectors using genetic engineering.

This object is achieved according to a first embodiment of the invention with vectors which comprise a nucleotide sequence of the general formula (I)

R-X-A-X-IRES-X-B-X-polyA  (I)

in which
R is a regulatory nucleotide sequence for a constitutive or inducible gene expression,
A is a gene coding for a protein which can induce a tumorigenic growth of cells,
IRES is a nucleotide sequence of viral, cellular or synthetic origin which is responsible in the stage of translation for the internal initiation,
B is a gene coding for a sensitively detectable, secreted protein,
poly(A) is a nucleotide sequence for the polyadenylation of the transcript and
X are optional linker sequences.

The vectors of general formula (I) are used if non-tumorigenic cell lines are to be altered by genetic engineering.

If cell lines are to be altered by genetic engineering which already have tumorigenic properties before the altering, the above-named object is achieved according to a second embodiment of the invention with vectors comprising a nucleotide sequence of the general formula (II)

R-X-B-X-IRES-X-C-X-polyA  (II)

in which
R is a regulatory nucleotide sequence for a constitutive or inducible gene expression,
B is a gene coding for a sensitively detectable, secreted protein,
IRES is a nucleotide sequence of viral, cellular or synthetic origin which is responsible in the stage of translation for the internal initiation,
C is a gene coding for a protein which makes possible a selection based on a resistance,
poly(A) is a nucleotide sequence for the polyadenylation of the transcript and
X are optional linker sequences.

The present invention describes the construction of novel, dicistronic expression vectors which couple the expression of a gene B coding for a reporter protein with that of a second gene A or C. This coupling takes place via an "internal ribosomal entry site" (IRES) which is placed between the two genes to be expressed. In distinction to the known, multicistronic expression units for the equimolar expression of heterodimeric proteins, e.g. PDGF-A/B (Dirks et al., Gene 128, 247–249, 1993; WO 94/05785, which also describes the IRES sequences coming into consideration), an equimolar expression is not obligatorily necessary according to the invention since the essential functional feature is the coupling of the protein synthesis of the reporter protein with that of a functionally interesting second protein.

According to a preferred embodiment of the invention the gene B codes for a secreted, alkaline phosphatase, especially for the secretable human, placenta-specific, alkaline phosphatase (SEAP). It is advantageous that SEAP is secreted by transfected cells and can therefore be demonstrated in culture supernatants. In addition, there are simple, very sensitive methods of demonstration based on chemiluminometric substrates (Bronstein et al., Anal. Biochem. 219, 169–181, 1994).

In the case of vectors comprising a second gene A, the latter preferably codes for cellular transformation. Genes A which code for a receptor tyrosine kinase (RTK) which can induce a tumorigenic growth of cells, especially for the receptor tyrosine kinase erbB2/HER2 are especially preferred.

If the vectors comprise a gene C, the latter preferably codes for an enzyme which inactivates a cytotoxic compound, especially for the enzyme amino glycoside-3'-phosphotransferase. Such C genes make possible a selection based on a resistance.

The vectors make it possible, for example, for vectors of general formula (I) with a coupling of a transforming gene with SEAP that its transcription/expression and therewith also the number of vital transformed cells to be quantified via the SEAP activity in culture supernatants in vitro and in vivo, for example, in serum. When using vectors of this type, a C gene coding, for example, for puromycin-N-acetyltransferase (Vara et al., Nucl. Acids Res. 14, 4617–4624, 1986), hygromycin-B-phosphotransferase (Blochlinger & Diggelmann, Mol. Cell. Biol. 4, 2929–2931, 1944) or amino-glycoside-3'-phosphotransferase (Colbere-Garapin et al., J. Mol. Biol 150, 1–14, 1981) is transferred by co-transfection into the target cell and makes possible a selection onto stably transfected cells.

For the expression of a gene in mammalian cells, the latter is used in the context of an appropriate expression vector for stable transfection. Such a vector for expression in mammalian cells contains a gene (or genes) under the control of corresponding genetic elements (promotor, polyadenylation signal, among others), and in accordance with the invention a regulatory nucleotide sequence R for a constitutive or inducible gene expression and a nucleotide sequence poly (A) for the polyadenylation of the transcript. The promotor element is either constitutively active, in which instance a promotor derived from SV-40 ("immediate early promotor" from SV-40) is especially advantageous, or it can be regulated in its activity with tetracycline or a derivative (Gossen & Bujard, Proc. Natl. Acad. Sci. U.S.A. 89, 5547–5551, 1992, WO 94/29442). The latter principle is functional in vivo in transgenic mice (Furth et al., Proc. Natl. Acad. Sci.

U.S.A. 91, 9302–9306, 1994). The present invention has the advantage that the principle can also be used in nude mice, for example, for subcutaneously transplanted, tumorigenic cells modified by genetic engineering (see FIG. 5).

Optional linker sequences X consist of linker sequences customary in cloning vectors, for example polylinkers, and contain for example cleavage sites for restriction endonucleases.

The technique of co-transfection is frequently used, that is, various expression vectors are transferred together into the target cell. This is especially the method of choice when the expression vector with the gene(s) to be expressed does not contain selection genes. A general survey of this topic as well as of the methods of the stable transfection of mammalian cells is offered by the monograph of M. Kriegler ("Gene Transfer and Expression", W. H. Freeman Inc. New York, 1990). If the gene is under the control of a regulatable promotor element the expression can be turned on or off. A very elegant tetracycline-regulated gene expression system is the one already mentioned above by Gossen and Bujard. The expression of a transforming gene in vitro and in vivo can be turned on or off via this inducible expression system and is quantifiable via the SEAP activity. It uses a fusion protein in the form of the tetracycline-controlled transactivator (tTA), which activates a minimal promotor via bonding to a specific tetracycline operator sequence. The tTA protein is separated from the operator sequence by the addition of tetracycline or derivatives and the gene expression is turned off therewith.

According to a further preferred embodiment of the invention, R accordingly comprises a tetracycline operator sequence and a minimal promotor. In particular, R constitutes the nucleotide sequence $tetO_7$/CMV.

According to the invention, mammalian cell lines are stably transfected with the vectors of general formula (I) or (II). Transfected mammalian cell lines representing the individual cell clones are especially preferred. Preferred examples for mammalian cell lines transfected in accordance with the invention are transfected NIH3T3 fibroblasts. In particular, tumor cell lines are transfected with the vectors of general formula (II) whereas other mammalian cell lines are altered to tumor cell lines by genetic engineering with the vectors of general formula (I).

The molecular biological techniques necessary for producing the vectors are described in detail in Maniatis et al. ("Molecular Cloning: A Laboratory Manual", 2nd edition, Cold Spring Harbor Laboratory/New York, 1992), Ausubel et al. ("Current Protocols in Molecular Biology", J. Wiley & Sons) as well as in the patents of Cohen et al. ("Process for Producing Biologically Functional Molecular Chimeras (by Genetic Engineering)", U.S. patent application Ser. No. 4,237,224) and Collins et al. ("Process for the Production of Hybrid Bacteria", U.S. patent application Ser. No. 4,304,863).

The invention also provides a method of screening antitumor drugs which comprises the following steps:

a) Construction of a vector of general formula (I) or (II), as described above, b) Stable transfection of a mammalian cell line with the vector obtained in step a), c) Growth of the mammalian cell line obtained in step b) in a mammalian tissue, d) Removal of a serum from the mammalian tissue obtained in step c) and e) Demonstration of the reporter protein in the serum obtained in step d).

The present invention describes the direct demonstration of SEAP from test animals (nude mice) which obtain implants of cells altered by genetic engineering. The demonstration of SEAP takes place, for example, using the serum of the animals which is repeatedly withdrawn from them during an experiment. This repeated withdrawal from the sublingual vein is not associated with any lasting effects on the test animal. The demonstration is possible in a highly sensitive manner—a photometric enzyme test using the substrate 4-nitrophenylphosphate or an even considerably more sensitive chemiluminometric demonstration using the substrate CSPD® (Tropix Inc.; Bronstein et al., Biotechniques 17, 172–177, 1994) is employed for measuring the SEAP activity. The background activity of phosphatases in the serum is negligibly small under the selected test conditions. A concentration effect is produced due to the implantation of a relatively large cell number associated with a low plasma volume. Even if transfected cells in vitro excrete only slight amounts of SEAP into the culture medium, it is multiply concentrated in the serum of the test animals and can therefore be readily demonstrated. However, this use does not have to be limited to SEAP; other genes coding for excreted reporter proteins such as, for example *Vargula hilgendorfii* luciferase are in principle suited for the method described in the invention. This also includes cDNA genes which are altered by genetic engineering and then code for a secreted protein, for example by appending a signal sequence and/or deletion of membrane-based sequences.

The present invention describes a novel method of determining the tumor mass ("tumor load") which takes place via the measuring of SEAP activity in the serum. The latter is secreted by the tumor-forming cells modified by genetic engineering and is thus transferred into the circulation of the blood. The direct quantitative detection of vital tumor cells is possible via the measuring of the SEAP activity in serum. There is a very good correlation with the tumor weight determined by palpitation (see FIG. 4). Tumor cells can be demonstrated in the animal already in this connection, although there is still no palpable tumor. Thus, the method described in the present invention permits a highly sensitive demonstration of the "tumor load" in vivo. Moreover, it is not limited to subcutaneous tumors but rather also makes it possible to monitor therapy experiments with metastasizing or orthotopically transplanted tumors of any kind. For example, the demonstration of orthotopically transplanted colon carcinoma cells in nude mice is shown by measuring SEAP activity in the serum of the animals in the present invention.

Experiments with cells altered by genetic engineering are shown in the present invention which make this precisely possible. In the invention, transfixed murine NIH3T3 fibroblasts which are transformed by overexpression of the receptor tyrosine kinase HER2 are shown in an example (see FIG. 3 and the literature of Hudziak et al., Proc. Natl. Acad. Sci. U.S.A. 84, 7159–7163, 1987 and DiFiore et al., Science 237, 178–182, 1987). According to the current state of knowledge, receptor tyrosine kinase HER2 is quite significant in the case of various human tumors (Slamon et al., Science 235, 177–182, 1987). In the model system described here the HER2 expression is transcriptionally coupled with the placental, alkaline phosphate secreted by humans (SEAP via an IRES sequence. Transfected NIH3T3 cells overexpressing HER2 are completely transformed according to generally recognized criteria (see also FIG. 3 and the data in table 1). The SEAP excreted by these tumorigenic cells can be demonstrated in very slight amounts in the serum of test animals (see FIG. 4A). Other thermally labile phosphatases contained in the serum are practically totally inactivated by a heat treatment of serum (30 min at 65° C.) and the addition of the inhibitor homoarginine. Only very slight amounts of serum are required for the measurement, e.g. 25 μl in a standard experiment. This can be multiply withdrawn during an experiment at certain time intervals from the Vena sublingualis without the test animal being lastingly affected. In the case of a subcutaneous model tumor, the tumor mass determined by palpitation displays thereby an excellent correlation with the SEAP activity determined in the serum of the test animals (see FIG. 4C). In another example the expression of receptor tyrosine kinase HER2 and, coupled therewith, of reporter protein SEAP can be turned off by transcription in vivo. The method of operation of the basic principle has already been discussed. The result is shown by way of example for an in-vivo experiment with a subcutaneous model tumor (see FIG. 5). Shortly after the injection of anhydrotetracycline the SEAP activity demonstrable in the serum decreases with linear kinetics. The tumor weight determined by palpation remains constant at approximately 0.1 g in all animals treated, that is, the growth of the tumor is stopped. The plasma half-life determined from this experiment for SEAP is approximately 28 h. This relatively short plasma half-life makes it possible to directly express a decrease of vital tumor cells in a therapy experiment by a lowering of the SEAP plasma activity. Such a therapy experiment could be performed in the present example of HER2 receptor tyrosine kinase in the application of an HER2 RTK-specific antagonist (tyrphostine). The start of the inhibition of protein tyrosine kinases in general and substances suitable to this end are well known in the literature (Levitzki & Gazit, Science 267, 1782–1788, 1995).

The present invention displays a novel combination and use of already known systems in the linking of the tetracycline-regulated expression system with dicistronic vectors and the coupling of a transforming protein such as HER2 to SEAP as reporter protein. The function of the expression system is to be monitored via the measuring of the SEAP activity in the serum of test animals after the administration of tetracycline or a derivative. At the same time, the relevance of the tumor-triggering gene for the growth of the solid tumor can be evaluated via the determining of the tumor growth by palpitation. This is quite significant for an evaluation of the significance of a target for the tumor therapy. Before suitable inhibitors of oncoprotein are found a transcriptional "knock-out" can be simulated in the model presented here. The significance of the oncoprotein in the creation of tumors and the further growth of the solid tumor can be studied in models by inhibition on the transcription plane with inclusion of the biological half-life of the oncoprotein. A further application is also addressed here. Cells transformed by stable transfection of an oncogene or by its dysregulated expression are not genetically stable in any manner desired. This applies in particular to murine fibroblasts such as NIH3T3 or also Rat1 cells. It is therefore very important when using cells altered in this manner by genetic engineering to continuously check the dependency of the transformed phenotype on the oncogene introduced. This is superbly possible in vivo with the tetracycline-controlled expression system described in the present invention. No tumors should develop during the injection of tumorigenic cells and the simultaneous administration of anhydrotetracycline in as far as the oncogene placed under the control of the inducible promotor element alone induces the tumorigenic growth in vivo. However, if further genetic defects occur in the course of the in-vitro culture ("second hits"), then tumors develop in the nude mouse even in the case of suppressed expression of the transforming gene.

However, the present invention is not limited to model cell lines such as NIH3T3 transformed by transfection. Rather, any tumor cells can be altered by genetic engineering in such a fashion that they excrete demonstrable amounts of SEAP. Tumor markers in the serum of cancer patients have long been used for diagnostic purposes. Note, for example, human chorionic gonadotrophin (hCG), acidic phosphatase, prostate-specific antigen (PSA) and also PLAP. Various forms of alkaline phosphatase can be demonstrated in human tumor cell lines, even thermally stable isoenzymes (Benham et al., Int. J. Cancer 27, 637 644, 1981). However, the expression is frequently membrane-based or intracellular. Little is known about the mechanism of the secreted expression observed in a few instances. However, it can be connected to the phosphatidyl inositol glycane linkage found for PLAP. As table 2 shows, a significant activity of thermally stable AP can be demonstrated in the culture medium in vitro in the minority of the selected tumor cell lines of very varied origin. By way of example it is shown that three tumor cell lines secrete significant amounts of SEAP after stable transfection with an appropriate expression vector. Even if a non-transfixed tumor cell line secretes thermally stable AP activity into the culture medium, the amount can be significantly raised by transfection.

An optimal tumor model in vivo takes into account the fact that the cancer cells in a tumor are in a complex interaction with the total organism, especially with the surrounding tissue. Paracrine stimulation of growth, tumor vascularization or cell-matrix interactions and metastasizing are cited here by way of example. In a subcutaneous tumor model these complex events can be simulated only to a very insufficient extent and are frequently not comparable to the physiological conditions. Moreover, only a part of human tumors actually grow to a solid tumor after subcutaneous implantation. A methodological alterative can be seen in the orthotopic transplantation of tumor cells. Here, the tumor material is transplanted directly into the organ of origin. The advantages of orthotopically transplanted tumors have been demonstrated, for example, for malignant melanomas, prostate tumors or osteosarcomas (Kerbel et al., Cancer & Metast. Rev. 10, 201–215, 1991; Stephenson et al., Natl. Cancer Inst. 84, 951–957, 1992; Berlin et al., Cancer Res. 53, 4890–4895, 1993). In the case or orthotopically transplanted tumors an evaluation of the success of a therapy is possible at this time only by determining the extension of life. However, if the tumor cells are altered by genetic engineering as described above, so that they synthesize SEAP, the growth of the tumor cells can be precisely determined by measuring the SEAP activity in the serum of the test animals. This is especially simple if the tumor cells used for the transplantation already secrete measurable activities of heat-stable phosphate themselves (see table 2, especially the KB cell line). An orthotopic transplantation experiment (FIG. 6C) in comparison to the subcutaneous tumor (FIG. 6 A/B) for the human, stably transfected colon adenocarcinoma cell line HT-29 is shown as a model. Thus, even orthotopic tumor models are accessible to a routine screening of antitumor drugs using the methods shown in the present invention.

Finally, the present invention can result in a rethinking of the use of animal tests with a consequent reduction in the number of test animals. The measuring of SEAP activity in the serum of test animals is possible in a very sensitive manner. For this reason the tumor cells become quantifiable before a tumor becomes macroscopically visible and palpable. A therapeutic test could thus start even before a tumor causes symptoms and problems. The success of a therapy can then be readily determined on the decrease of the SEAP activity in the serum. The troublesome effect of a solid tumor for the test animal would thus be limited to a minimum. Moreover, multiple therapy cycles could be conceived which correspondingly reduce the number of test animals normally necessary for a test which can be statistically evaluated.

The use of the present invention can be summarized as follows.

(i) Model- or tumor cell lines are altered by genetic engineering in such a manner that they synthesize and excrete SEAP. The latter can be sensitively demonstrated in the serum of tumor-carrying test animals and correlates with the tumor mass. It is possible thereby to determine the number of vital tumor cells in test animals via the SEAP activity in the serum. This makes possible an exact monotoring of therapeutic experiments with potential antitumor drugs using any desired tumor models.

(ii) The relevance of any transforming gene for the creation of tumors and the growth of a solid tumor can be studied as a model by using dicistronic expression vectors with SEAP as reporter gene as well as using an expression system which can be regulated with tetracycline. The effect of an antagonist which is still to be discovered can be simulated by a transcriptional "knock-out" in vivo and the further strategy significantly influenced thereby.

The present invention is therefore used preferentially in the screening of potential antitumor drugs in vivo and in the target validation before such a screening.

BRIEF DESCRIPTION OF THE FIGURES

FIGS. 3E and 3F show that cell clones overexpressing HER2 in the foci assay show a transformed phenotype.

FIGS. 3G and 3H show that, in the case of HER2 expression turned off correspondingly by anhydrotetracycline, the transformed phenotype is reverted.

FIGS. 5A–5C show that the number of vital tumor cells can be very sensitively quantified via the SEAP activity in the serum and correlates up to the time of injection of anhydrotetracycline (test day 28) with the tumor mass determined by palpitation.

DETAILED DESCRIPTION OF THE INVENTION

Figure 1A:
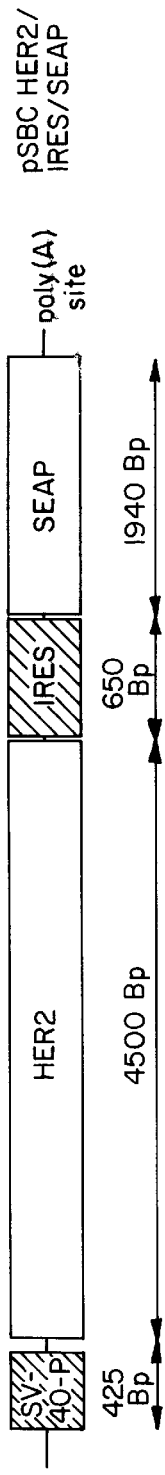
FIGS. 1A–1D show the construction of the vectors used in the present invention in a summarized fashion and is to be understood as being exemplary.

The invention is explained in detail in the following using examples intended to illustrate how vectors with the SEAP gene can be used for stable cell transfection and how cells altered with the vectors by genetic engineering are used for in vivo experiments with xenotransplants in nude mice for the sensitive determination of the mass of vital tumor cells. Likewise, it is shown in model experiments how the invention is used for the sensitive detection of orthotopically transplanted tumors.

EXAMPLE 1

Dicistronic Expression Vectors with SEAP

The expression vectors used for the various experiments are described in the following and the methods required for their production are named by way of example.

Methods

Standard methods of molecular biology were used for the cloning experiments which methods are described in detail in, among other places, Ausubel et al., Current Protocols in Molecular Biology, J. Wiley & Sons 1989 and Maniatis et al., ("Molecular Cloning: A Laboratory Manual", 2nd edition, Cold Spring Harbor Laboratory/New York, 1992).

For the DNA analysis restriction endonucleases of the type II in the appropriate buffer (e.g. 6 mM tris pH 7.5, 6 mM $MgCl_2$, 100 mM NaCl, 0.4 mg/ml BSA, 0.002% $NaN_3$) were incubated with 1–10 μg plasmid DNA at 37° C. After an appropriate incubation time of, for example, 3 h the specimens are separated by gel electrophoresis.

This separation of DNA fragments after fragmentation by restriction enzymes takes place in agarose gels with a concentration of 0.8–2% (w:v) as a function of the size of the DNA to be analyzed. A size standard is used to determine the size of linear DNA fragments in base pairs (Bp) (e.g. λ-DNA BstEll cut). TAE buffer (40 mM tris acetate, 1 mM EDTA, 0.5 mg/l ethidium bromide) is used as run buffer for the electrophoresis. The run takes place at a constant voltage of, for example, 200 V using a gel chamber with a size of 35.5×18 cm. After the end of the run the gel is removed with the gel carrier and the DNA rendered visible on a transilluminator under UV stimulation.

The covalent linking of DNA fragments is catalyzed by the DNA ligase of phage T4. After cutting the DNA with the appropriate restriction enzyme(s) and separation in a NuSieve LMP ("low melting point") agarose gel in TAE buffer, the desired DNA fragment is cut out of the gel and melted at 70° C. A typical ligation batch consists of 1 μl vector DNA, 2–4 μl DNA fragment(s), 5 μl 10× ligation buffer (500 mM tris pH 7.5, 100 mM $MgCl_2$, 100 mM DTT, 10 mM rATP, 250 μg/ml BSA), 1 μl T4 DNA ligase (400 units/μl) in 50 μl total volume. After approximately 3 h incubation at 25° C. chemocompetent cells from *Escherichia coli* K12 strain MC 1061 (Wertmann et al., Gene 49, 253–262, 1986) are transformed. To this end, appropriately pretreated cells stored at −80° C. are thawed and an aliquot of the ligation batch added to e.g. 100 μl cellular suspension and thoroughly mixed. After an incubation of 15 min on ice the specimens are incubated for 5 min at 37° C. in a water bath and again placed on ice. The matter is now spread out on agar plates of LB medium (0.5% w:v bacto-trypton, 1% w:v yeast extract, 0.1 M NaCl) with an appropriate antibiotic (usually 200 μg/ml ampicillin). The plates are incubated overnight in the incubator and individual clones subsequently analyzed.

For the analytic isolation of plasmid DNA by alkaline cell lysis (Birnboim & Doly, Nucl. Acids Res. 7, 1513 1523, 1979), 1.5 ml of an overnight culture is taken at 37° C. of the clone to be characterized in LB medium (with antibiotic). After pelletization of the E. coli cells, the supernatant is removed, the cellular pellet resuspended in 200 µl 10 mM EDTA solution pH 8 and 400 µl denaturing buffer (0.2N NaOH, 1% w:v SDS) and 300 µl potassium acetate buffer (5M KAcO pH 4.7) added one after the other. The reaction vessels are agitated and centrifuged for pelletization of the precipitate. The supernatant is transferred into a new reaction vessel and extracted with 500 µl neutral phenol (phenol equilibrated in 0.1M tris pH 7.5). The supernatant is removed after extraction and the plasmid DNA contained precipitated with isopropanol. The dried DNA is dissolved in 50 µl TE buffer with RNAse (5 mM tris pH 8.01 mM EDTA, 20 µg/ml RNAse). A similar procedure is used in principle for the preparative isolation of DNA, but with appropriately larger amounts. In addition, purification of the plasmid DNA takes place with caesium chloride density-gradient centrifugation. The quantification of isolated plasmid DNA is performed by taking a UV spectrum (wavelength 220–300 nm). An $Abs_{260\ nm}=1$ thus corresponds to an amount of 50 µg double-stranded DNA.

Result The vectors pSBC1 and pSBC2 used for the cloning experiments as well as corresponding derivatives pSBC1 SEAP and pSBC2 SEAP were first described by Dirks et al., (Gene 128, 247–249, 1993). For the dicistronic expression of the HER2 receptor protein the HER2 cDNA was isolated from the vector pCOB213 (Yamamoto et al., Nature 319, 230–234, 1986) via [digestion] with MluI and ligated after filling with Klenov polymerase into vector pSBC1 opened with SmaI. The resulting construct pSBC1 HER2 was combined via digestion with AseI/NotI with pSBC2 SEAP, which gives rise to the dicistronic construct pSBC HER2/IRES/SEAP (FIG. 1A). In this vector the expression of the HER2 protein, which transforms fibroblasts after overexpression, is coupled via the IRES sequence to the reporter SEAP. The expression takes place constitutively under control of the "immediate-early promotor" of SV-40.

Figure 1B:
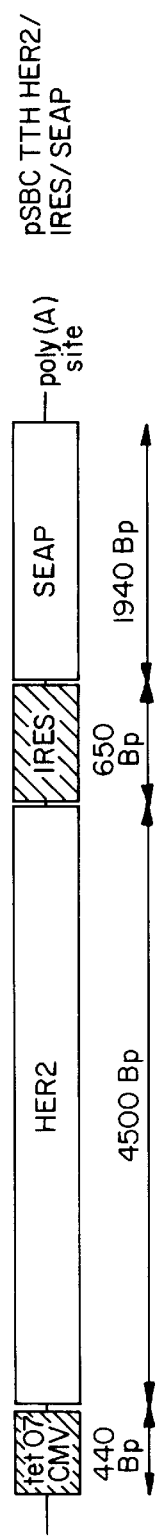

A modified vector pSBCTTH1 was used for the corresponding construct with a promotor regulatable with tetracycline (or derivative). This vector contains instead of the SV-40 promotor/enhancer sequences of pSBC1 the $tetO_7$/CMV minimal promotor sequence from pUHC13-3 (Gossen & Bujard, Proc. Natl. Acad. Sci. U.S.A. 89, 5547–5551, 1992). The recloning of the HER2 cDNA from pSBC1 HER2 took place via EcoRI/EcoRV/NotI into the EcoRI/NotI opened vector pSBCTTH1 and results in the construct pSBCTTH1 HER2. The latter was combined as described above via AseI/NotI with pSBC2 SEAP, resulting in the inducible dicistronic construct pSBCTTH HER2/IRES/SEAP (FIG. 1B).

Figure 1C:
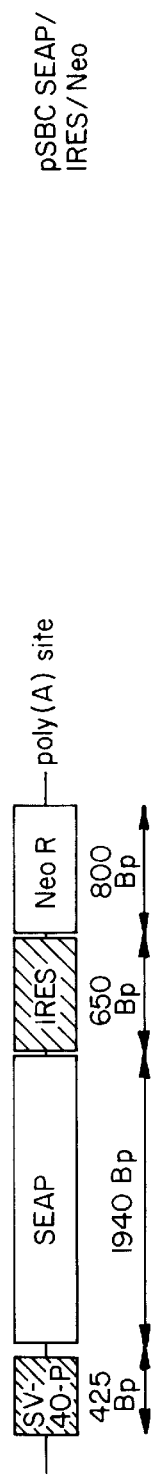
Figure 1D:
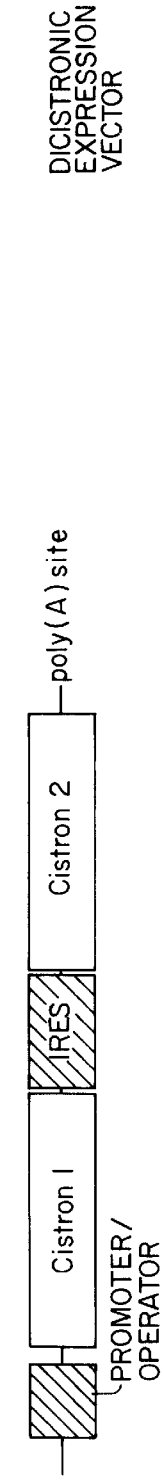

The region coding for the protein was amplified from the vector pAG60 (Colbere-Garapin et al., J. Mol. Biol. 150, 1–14, 1981) by means of PCR from the cDNA coding for the enzyme amino glycoside-3'-phosphotransferase type 2. The enzyme amino glycoside-3'-phosphotransferase imparts a resistance to the antibiotics kanamycin or neomycin and also to the gentamicin derivative geneticin, which is toxic, among other things, for mammalian cells (G418®). The gene was correspondingly cloned into pSBC2 by means of the cleavage cites EcoRI/HindIII contained in the oligonucleotide primers used for the PCR. The construct PSBC SEAP/IRES/Neo$^R$ is produced by a recloning via AseI/NotI into vector pSBC1 SEAP, as already described above (FIG. 1C).

The construction of the vectors used in the present invention is shown in FIG. 1 in a summarized fashion and is to be understood as being exemplary. Any transforming gene can be placed in cistron 1—e.g. pSBC oncogene/IRES/SEAP— or any resistance gene in cistron 2—e.g. pSBC SEAP/IRES/resistance gene (figure ID). The promotor-/operator element—constitutive or inducible—is to be understood in a correspondingly variable manner.

EXAMPLE 2

Highly Sensitive Determination of the SEAP Activity

The methods for the demonstration of SEAP activity from cell-culture supernatants in vitro as well as from serum in vivo are described in the following. These methods are used for the sensitive detection of SEAP. Phosphatase (PLAP) of a defined activity purified from human placenta is used for detection.

Methods

Obtaining serum from test animals. Approximately 300 µl whole blood is drawn from the vena sublingualis for the determining of SEAP activity in the serum of nude mice. The whole blood is allowed to coagulate for 20 min at 40° C. and is then centrifuged for 10 min at 40° C. in a Heraeus biofuge 15R at 4500 rpm. The supernatant is removed and the matter re-centrifuged for 3 min under the same conditions. After the second centrifugation, the serum can be used directly for the determination of activity or stored at −20° C. In a corresponding fashion, cell-culture supernatant is taken from in vitro cell cultures at defined times for the determination of SEAP activity. Any cell fragments contained therein are pelletized by centrifugation for 5 min at 4500 rpm in a Heraeus biofuge 15R.

Phospha-Light® chemiluminescence reporter gene assay (Bronstein et al., Biotechniques 17, 172–177, 1994). The phospha-Light® assay (Tropix Inc.) is used for the chemiluminometric determination of SEAP activity with CSPD® as substrate. This method is highly sensitive and suitable for the demonstration of very slight amounts of enzyme. Depending on the test, 15 µl serum or cell-culture supernatant are pipetted directly to 50 µl dilution buffer in a 96 well microtiter plate for luminescence measurements (Dynatech), incubated for 30 min at 65° C. and then placed on ice to cool. After the addition of 50 µl test buffer, the matter is incubated for 5 min at 30° C. The measurement is started by the addition of 50 µl reaction buffer (composition of the reaction mixture: 50 mM $NaCO_3$ pH 9.5, 10 mM homoarginine, 1 mM $MgCl_2$, EMERALD amplifier, CSPD substrate). The measurement device used is a microtiter plate luminometer type MicroLumat LB 96 P (EG & B Berthold). The measurement interval is 3 min and 3 (6) measurements take place. The maximum light emission is achieved approximately 6 min (when measuring SEAP activity from serum after approximately 15 min) after the addition of the reaction buffer.

SEAP activity is measured using p-nitrophenylphosphate as substrate. The assay measures the hydrolysis of p-nitrophenylphosphate to nitrophenol (absorption maximum at 405 nm, pH 9.8). Cell-culture medium or serum from nude mice pretreated as described above is used for the measurements. 100 µl of enzyme solution is incubated for 5 min at 65° C. in a water bath and then centrifuged for 2 min at 15000 rpm in a Heraeus biofuge 15R. The supernatant is used for the enzyme test, during which a typical reaction batch for microtiter plates is composed from 150 µl 1×SEAP-buffer (1M diethanol amine pH 9.8, 0.5 mM $MgCl_2$, 10 mM homoarginine), 50 μl 2×SEAP-buffer (2M diethanol amine pH 9.8, 1.0 mM $MgCl_2$, 20 mM homoarginine) and 50 μl cell-culture medium or serum. The reaction is started by the addition of 25 μl substrate solution (120 mM p-nitrophenylphosphate in 1×SEAP buffer). Measurement of the absorption at 405 nm (25° C. room temperature) takes place 5 min after the addition of the substrate in a Beckman microtiter plate photometer, type biomek plate reader.

In order to record corresponding standard curves, alkaline phosphatase of a defined activity purified from human placenta (Calbiochem) is used under the test conditions used in the enzyme test. The calculation of the enzymatic activity in m units/ml takes place from the recorded standard curves (see FIG. 2), with a "unit" (abbreviated "U") defined as the amount of enzyme which hydrolyses 1.0 μmole p-nitrophenylphosphate (PNPP) at 30° C. and pH 10.15 to p-nitrophenol.

Result

Figure 2A:
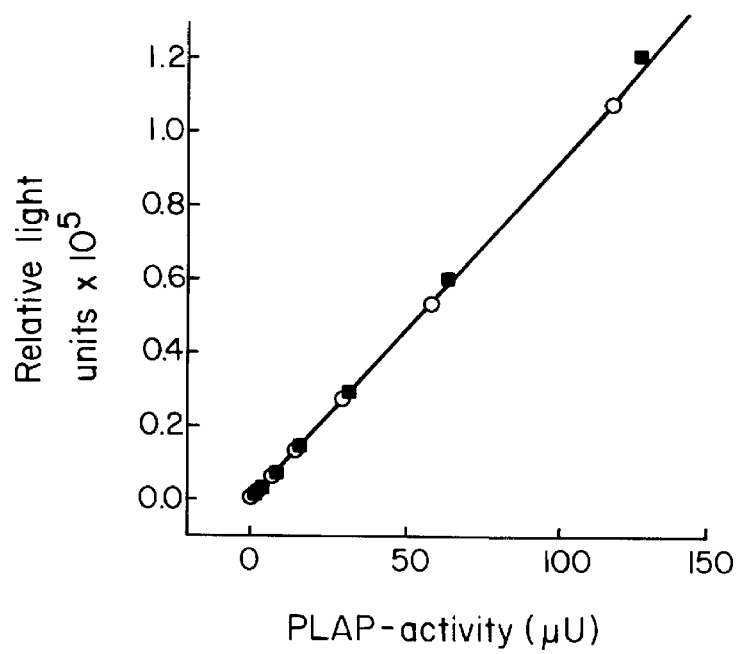
FIGS. 2A and 2B show sections of the corresponding calibration curves for determining the activity of SEAP from serum or cell-culture medium by means of chemiluminometric (FIG. 2A) or photometric assay systems (FIG. 2B).
Figure 2B:
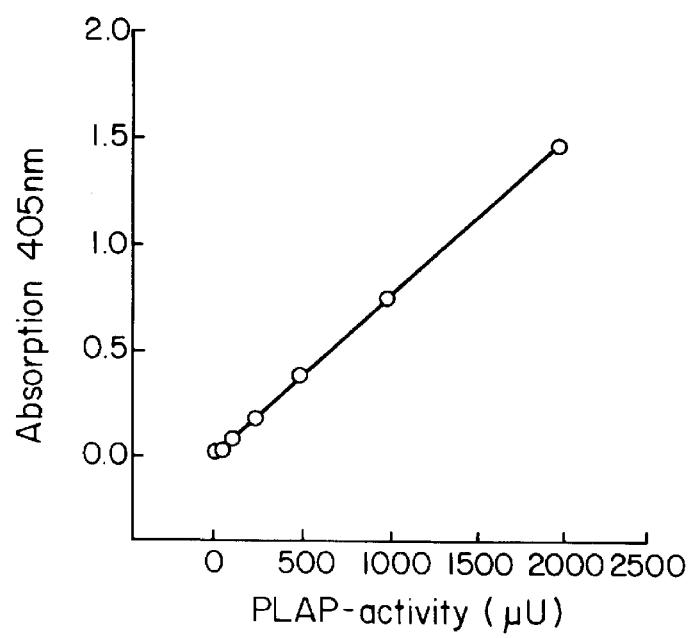

FIG. 2 shows sections of the corresponding calibration curves for determining the activity of SEAP from serum or cell-culture medium by means of chemiluminometric (FIG. 2A) or photometric assay systems (FIG. 2B). The linear measuring range of the photometric enzyme test is approximately ≈100μ units to ≈2000μ units PLAP. The maximum sensitivity of the test is approximately 100μ units PLAP/ml under standard conditions but can be improved even more by raising the incubation temperature and/or extending the measuring times. The chemiluminometric enzyme test has a linear measuring range of ≈0.06μ units to ≈500μ units PLAP. The maximum sensitivity under standard conditions is approximately ≈0.4μ units PLAP/ml. For determining the enzymatic activity in specimens with very high SEAP activities an appropriate dilution is carried out in the incubation medium.

EXAMPLE 3

Stable Transfection of NIH3T3 Fibroblasts

The methods used for the stable transfection of the NIH3T3 cell line (ATCC CRL 1658) are described in the following in which connection a clone modified starting from the named cell line and with the designation "NIH 3T3 clone H.3" was deposited in the German Collection of Microorganisms and Cell Cultures (DSM), D-38124 Braunschweig. Moreover, the analytics of the cell lines resulting therefrom on the transformation-specific parameters focus- and colony formation is shown.

Methods

Stable transfection by means of lipofection. The lipofectamin® reagent (Gibco BRL) is used for the transfection of NIH3T3 cells. The subsequently indicated amounts refer to a 25 $cm^2$ cell-culture flask. One day before the transfection, the cells in a cell density of $1-3\times10^5$ are uniformly exposed in normal culture medium (DMEM 4.5 g/l glucose, 10% v:v calf serum) (density at the time of transfection 50%–80% confluence). The following solutions are prepared for the transfection: Solution A: 6 μg co-transfer DNA and 0.6 μg selections DNA in 300 μl serum-free medium; solution B: 12–36 μl Lipofectamin® in 300 μl serum-free medium. Both solutions are thoroughly mixed and incubated for 15 min–45 min at room temperature, during which the DNA-liposome complex forms. 2.4 ml serum-free medium is then added per batch while the cells are washed with 6 ml serum-free medium. After removal of the entire cell-culture medium by suction, the cells are coated with the DNA-liposome complex. After 5 h incubation in an incubator at 37° C. and 5% $CO_2$, 3 ml serum-containing culture medium is added. The following day the cells are subjected to passages 1:20 to 1:40 in fresh culture medium. On the third day after the transfection the selection in the medium is begun with 125 μg/ml hygromycin B. The number of individual clones is determined, as soon as they can be recognized, in a phase-contrast microscope.

"Focus-formation assay" for transfected NIH3T3 fibroblasts (Riedel et al., Proc. Natl. Acad. Sci. U.S.A. 85, 1477–1481, 1988). The cells to be tested are cultivated to a maximum cell density of an 8.5 $cm^2$ cell-culture plate. After achievement of a confluent cell layer the medium is changed every 3–4 days without destroying the cell layer thereby. If cell clumps appear with cells which no longer grow in a contact-inhibited manner ("foci"), they are fixed and stained with methyl violet and counted. Alternatively, the cells can also be stained after fixing with a specific monoclonal antibody. Appropriate cloning cylinders are used for the isolation of the cells from a focus.

Cell growth in semisolid medium ("colony assay", Hamburger & Salmon, Science 197, 461–463, 1977). The test for determining the growth in semisolid medium consists of various agar layers in 8.5 $cm^2$ culture dishes: Layer 1 consists of 1 ml cell-culture medium with 0.5% (w:v) agar, layer 2 consists of 1 ml of a monocellular suspension ($2\times10^4$ cells/ml) in cell-culture medium with 0.25% (w:v) agar; layer 3 consists of 1 ml PBS and prevents the agar from drying out. The incubation period in the incubator at 37° C., 5% $CO_2$ is approximately 21 days. The determination of the colony number takes place under a binocular.

Result

The analysis of various stably transfixed NIH3T3 cells with, among other things, the vectors shown in FIG. 1 is summarized in table 1. The NIH3T3 fibroblasts stably transfixed as control without dicistronic vectors contain in the culture medium an SEAP activity which is low with 0.01 mU/ml and is on the demonstration boundary of the chemiluminometric enzyme test. The NIH3T3 cells transfixed for control with the construct pSBCTTH SEAP secrete 3.18 mU/ml SEAP into the culture medium but form neither foci nor colonies, that is, are not transformed. A comparable result regarding the SEAP activity contained in the medium is obtained in the analysis of NIH3T3 cells transfixed with the construct pSBC HER2/IRES/SEAP (9.30 mU/ml). However, the cells are transformed, as is clearly shown in the focus formation test.

The clonal mixture of NIH3T3 cells which were transfected with the inducible, dicistronic construct pSBCTTH HER2/IRES/SEAP secrete 1.08 mU/ml SEAP and form foci but no colonies. An individual cell clone 12.3/G8 isolated out of a focus secretes 10.16 mU/ml SEAP and displays both focus formation as well as colonies in soft agar, comparable to a further individual clone 12.3/H3 which secretes 26.16 mU/ml SEAP. The regulation of the expression by tetracycline (conc. 1 μg/ml) or its derivative anhydrotetracycline (conc. 10 ng/ml) in vitro is also shown. The expression of the reporter SEAP is practically totally turned off by the addition of the antibiotics and the transformation is likewise reverted (no formation of colonies or foci). It was shown in control experiments that the antibiotic has no significant antiproliferative effect in vitro in the concentrations used.

Figure 3A:
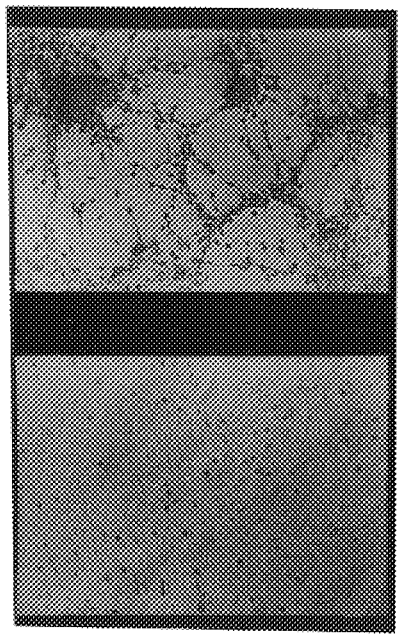
FIGS. 3A and 3B show the expression of the receptor tyrosine kinase HER2 by demonstration by means of the HER2-specific monoclonal antibody 9G6.
Figure 3B:
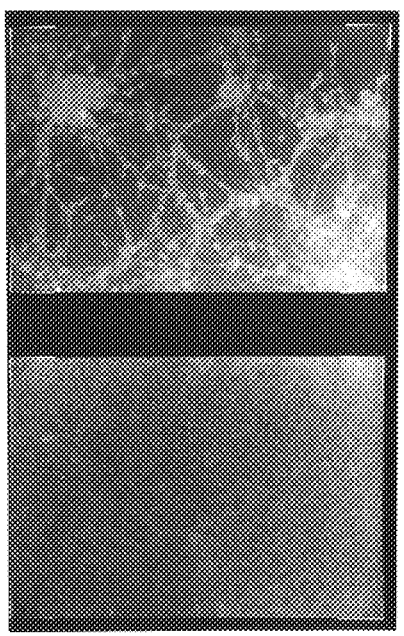
Figure 3C:
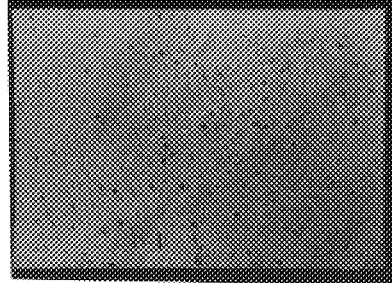
FIGS. 3C and 3D show that HER2 expression can be turned off by anhydrotetracycline.
Figure 3D:
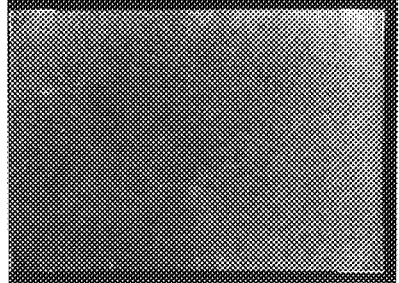

FIGS. 3 A/B show the expression of the receptor tyrosine kinase HER2 by demonstration by means of the HER2-specific monoclonal antibody 9G6 (phase contrast in FIG. 3B, fluorescence in FIG. 3B; 100× magnification). The HER2 expression can be turned off by anhydrotetracycline (phase contrast in FIG. 3C, fluorescence in FIG. 3D; 100× magnification). Cell clones overexpressing HER2 in the foci assay (FIG. 3 E/F; 32/100× magnification) show a transformed phenotype. In the case of HER2 expression turned off correspondingly by anhydrotetracycline, the transformed phenotype is reverted (FIG. 3 G/H; 32/100× magnification).

The following conclusions can be drawn from these experiments:
(i) NIH3T3 cells overexpressing HER-2 are transformed
(ii) The expression of the reporter gene SEAP or the stable transfection alone do not lead to a cellular transformation
(iii) HER-2 and SEAP are expressed coupled in HIH3T3 cells
(iv) The expression of HER2 and SEAP can be inhibited when using the inducible promotor by culture in medium with tetracycline or a derivative
(v) The cellular transformation induced by HER2 expression is reversibly inducible.

EXAMPLE 4

Figure 4A:
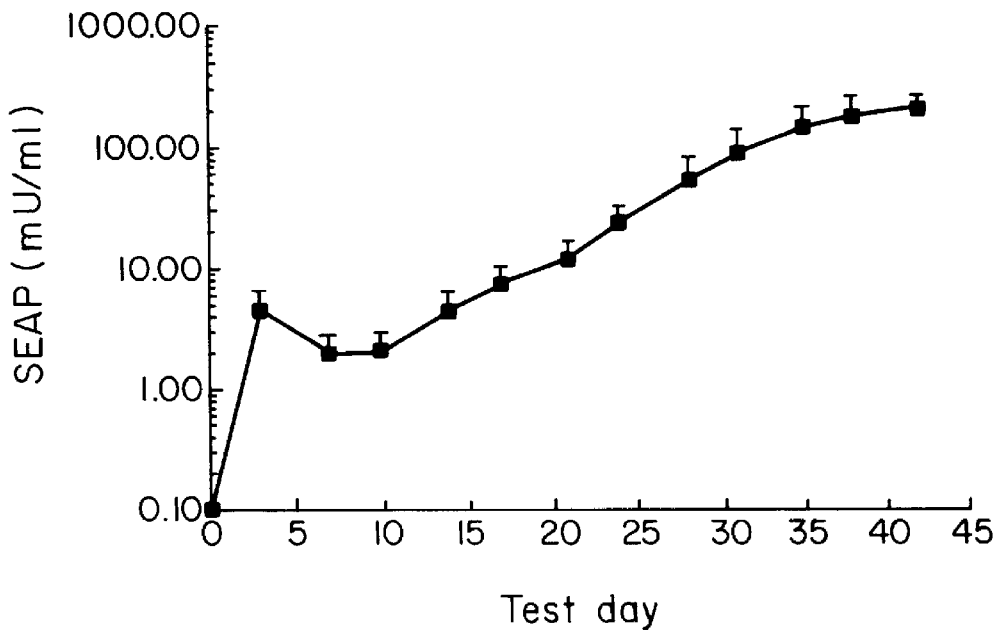
FIG. 4A shows that SEAP activity can be readily demonstrated in the serum with 4.66 mU/mil (average from n=5) 3 days after injection of the cells.
Figure 4B:
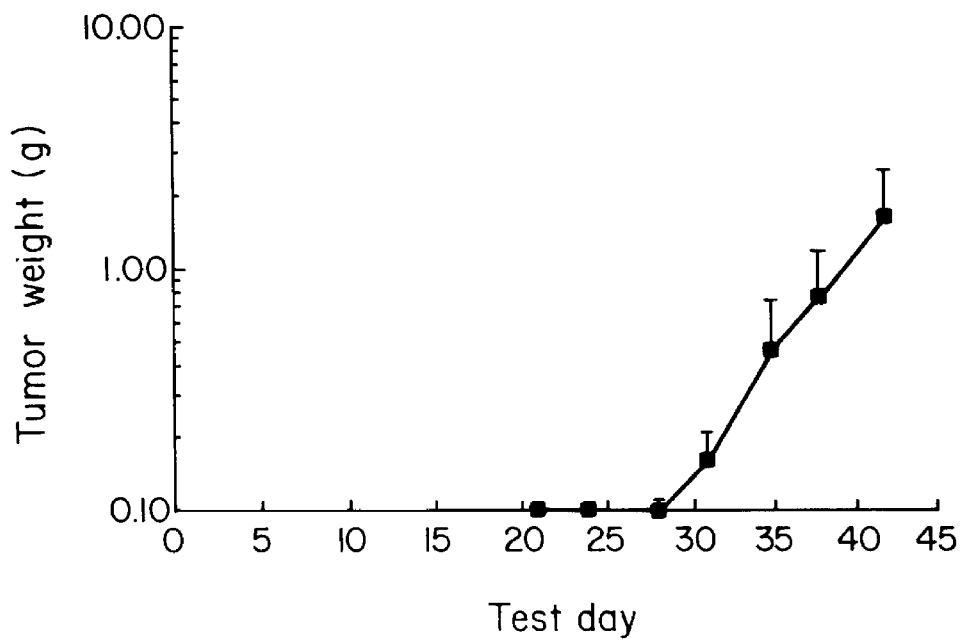
FIG. 4B shows the correlation of the tumor weight determined by palpitation with the SEAP activity measured in the serum.
Figure 4C:
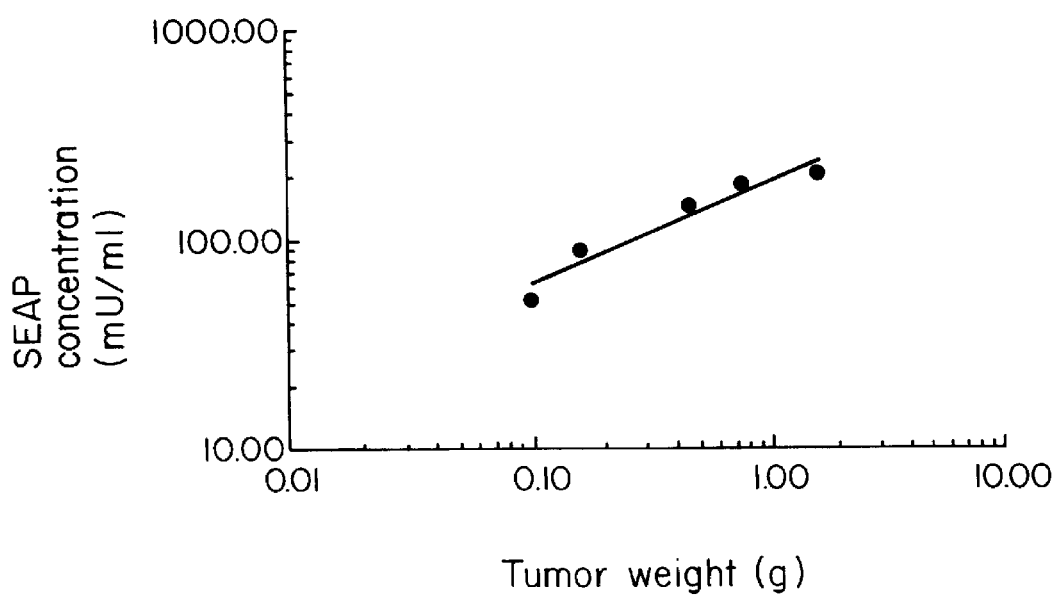

Sensitive Demonstration of the "Tumor Load" of NIH3T3 Fibroblasts Overexpressing HER2 by Determining the Activity of SEAP from Serum Nude mice in which cells of the NIH 3T3 individual-cell clone 12.3/H3 were subcutaneously implanted are used for the test. This individual-cell clone was isolated from NIH 3T3 cells stably transfected with the construct PSBC TTH HER2/IRES/SEAP. The formation of the subcutaneous tumor is shown as a function of the time with the measurement parameters tumor mass and SEAP activity in the serum of the test animals.
Methods Tumorigenity testing in nude mice. Female nude mice of the strain NMRI nu/nu are used for the demonstration of tumorigenity of various cell lines using the formation of subcutaneous, solid tumors. After a quarantine time of 4 weeks the animals are divided into groups and marked by ear piercing. In order to determine the basal SEAP activity in the serum approximately 300 µl whole blood is taken from the vena sublingualis of each animal, the serum extracted from it and the SEAP activity is determined (see example 2). The cell implantation takes place by means of subcutaneous injection into the right flank of the test animal. For example, 1×10$^6$ cells (for tests with NIH3T3 cells) are applied in a volume of 200 µl PBS per animal. 1 ml tuberculin syringes and # 16 cannulas are used for the application. During the test period of approximately 50 days the animals are checked twice weekly. In this check the body weight is determined, a blood sample taken and the tumor weight palpatorily quantified by comparison with a standard plasticine model. If no tumor can be felt 50 days after cell implantation or if the reporter gene can not yet be demonstrated in the serum, the test is terminated. Animals with exulcerated tumors or with a tumor weight above 4 g as well as animals with significant losses of body weight or in poor general condition are prematurely killed. An autopsy is performed on the killed animals and they are macroscopically evaluated. Organ changes, the nature of tumors and any metastases formed are registered. The tumor tissue removed from the test animals can be, as required, fixed, quick-frozen in liquid nitrogen or worked up for an in vitro cultivation.
Result FIG. 4A shows the SEAP activity (in mU/ml) which can be demonstrated in the serum as well as the tumor mass (in g) determined by palpation against the test time (testing period in days). Only a low, heat-stable phosphatase activity can be demonstrated in the serum of control animals and is subtracted from the measured values. It is apparent from FIG. 4A that SEAP activity can be readily demonstrated in the serum with 4.66 mU/ml (average from n=5) 3 days after injection of the cells. A palpable tumor (≧0.1 g) does not become visible until after a testing period of 21 days. The growth of the tumor becomes clear in all animals from the increase of the SEAP activity in the serum of the animals. The correlation of the tumor weight determined by palpation with the SEAP activity measured in the serum is shown in FIG. 4B and is very significant. It can thus be concluded from this test that
(i) A heat-stable phosphatase activity can be demonstrated only in a slight amount in the serum of nude mice,
(ii) SEAP excreted from transfixed, tumorigenic cells can be measured sensitively in vivo from drawn serum,
(iii) The SEAP activity quantified from the serum correlates very well with the tumor weight and
(iv) A measuring of vital tumor cells is possible even if no tumor can be palpated yet.

EXAMPLE 5

Figure 5A:
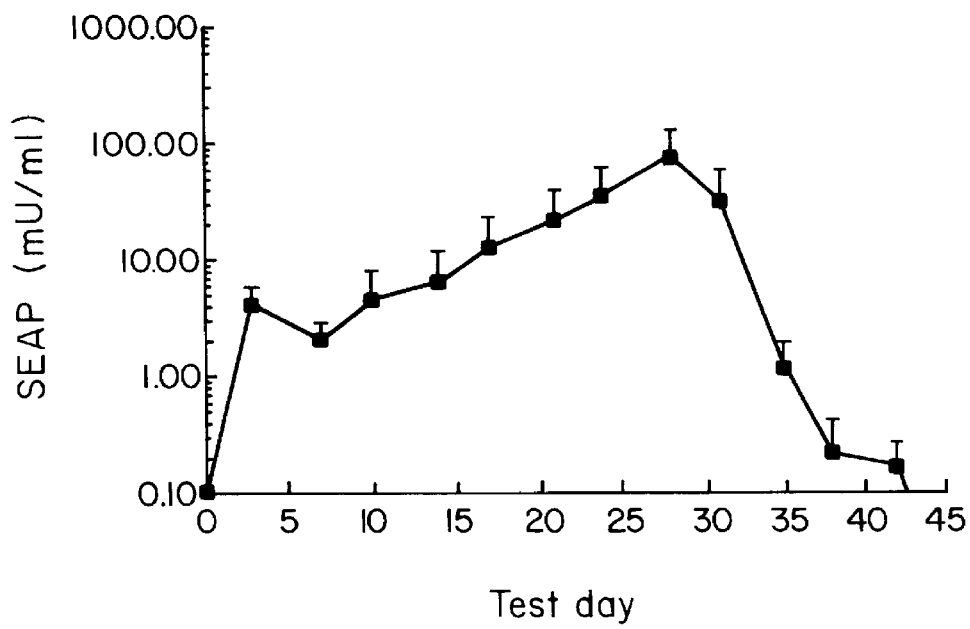
Figure 5B:
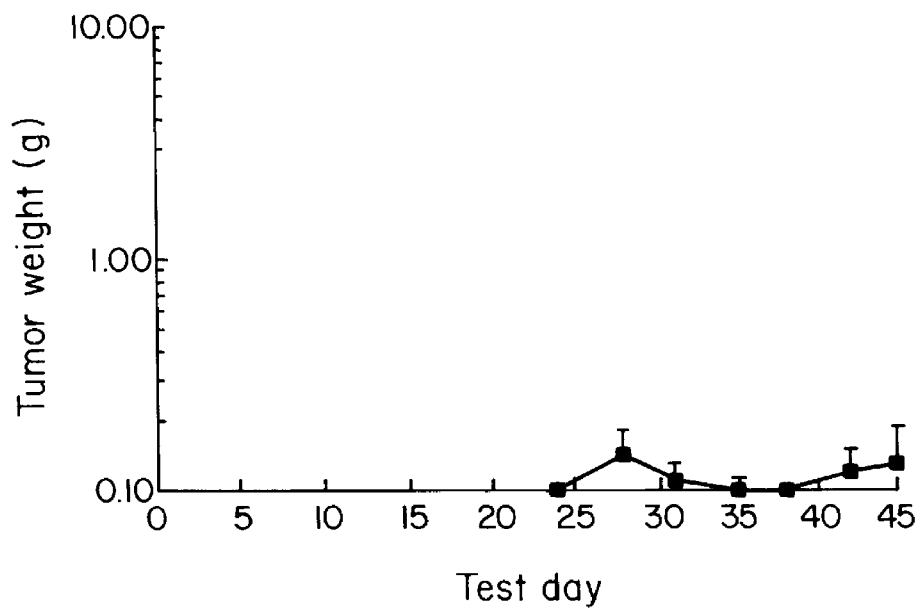

Tetracycline-Regulated Expression in Fibroblasts Altered in vivo by Genetic Engineering Nude mice in which cells of the NIH 3T3 individual-cell clone 12.3/H3 were subcutaneously implanted are used for the test. This individual-cell clone was isolated from NIH 3T3 cells stably transfected with the construct PSBC TTH HER2/IRES/SEAP. The formation of the subcutaneous tumor is shown as a function of the time with the measuring parameters tumor mass and SEAP activity in the serum of the test animals. On test day 28 anhydrotetracycline was injected in the animals upon palpation of tumors ≧1 g in order to turn off the expression of HER2 and SEAP.
Methods Treatment of the animals with anhydrotetracycline. A dose of 10 mg/kg three times weekly is applied subcutaneously for a treatment within the framework of a tumorigenity test. The LD$_{50}$ of anhydrotetracycline i.p. is 100 mg/kg thereby. The anhydrotetracycline solution is prepared in a concentration of 1 mg/ml in PBS and stored in an aliquoted manner at −20° C. Depending on the question posed, the treatment with anhydrotetracycline is started either directly after cell implantation or not until after the occurrence of tumors.
Result As FIG. 5 shows, the number of vital tumor cells can be very sensitively quantified via the SEAP activity in the serum and correlates up to the time of injection of anhydrotetracycline (test day 28) with the tumor mass determined by palpation. This corresponds to the results shown in example 4. The transcription of the dicistronic mRNA is turned off by the injection of anhydrotetracycline. This is demonstrated by the linear decrease of SEAP activity in the serum of treated animals (FIG. 5A). The activity of heat-stable phosphate in the serum is only slight on test day 38 with 0.22 mU/ml and on test day 45 it has been reduced to amounts which can no longer be demonstrated in all the animals. Moreover, it can be concluded from the direct transition and linear course of the two curves (SEAP activity before/after treatment) that anhydrotetracycline inhibits very rapidly and effectively transcriptionally. The plasma half life of SEAP can be determined with approximately 28 h from the linear course of the SEAP activity in the serum after the injection of anhydrotetracycline. This is of great importance for the use as reporter for a therapy test. In the experiment shown such a therapy experiment was practically simulated. A proliferation stop occurs under the selected test conditions and within the test time of 45 days. The tumor weight remains constant at approximately 0.1 g. In parallel experiments anhydrotetracycline was injected simultaneously with the injection of the cells altered by genetic engineering. Only marginal SEAP activities can be demonstrated in the serum in these test animals and in no instance does a palpable tumor develop.

EXAMPLE 6

Stable Transfection of Various Tumor Cell Lines

Various tumor cell lines suitable for a subcutaneous or orthotopic transplantation on a nude mouse were tested for heat-stable phosphatase activity in cell-culture supernatants. By way of example the tumor cell lines HT29 (ATCC HTB 38), KB (ATCC CCL17) AND OVXF 899L were stably transfected with the dicistronic construct pSBC SEAP/IRES/Neo$^R$, a clone modified starting from the cell line HT29 and with the designation "HT29 transfection H 20.2" was deposited in the German Collection of Microorganisms and Cell Cultures, D-38124 Braunschweig, and the activity of SEAP in culture supernatants determined. Specifically, the following tumor cell lines are involved:

HT-29 (ATCC HTB 38; Fogh & Trempe, in: Human Tumor Cells in vitro, 115–159, Plenum press, New York, 1975), an adenocarcinoma cell line of the colon, OVXF 899L (Licht et al., Proc. Amer. Assoc. Cancer Res. 31, A2210, 1990), an ovarian carcinoma cell line, SK-BR-3 (ATTCC HTB 30), a cell line from an adenocarcinoma of the breast, KB (ATCC CCL 17; Eagle, Proc. Soc. Exp. Biol. Med. 89, 362, 1955), a cell line from a carcinoma of the buccal mucous membrane, LXFA 629L, an adenocarcinoma of the lung, MEXF 514L (Licht et al., Journal of Cancer Research and Clinical Oncology, 118(2), 1992, 116–122), a cell line from a malignant melanoma, AR42J (ATCC CRL 1492), a cell line from a carcinoma of the exocrine pancreas of the rat, GH3 (ATCC CCL 82.1: Endocrinology 82, 342–352, 1968, a cell line from a pituitary tumor of the rat.

Except for the last two cell lines cited, AR42H and GH3, these are exclusively cell lines established from human tumors.

Methods

The determination of activity of heat-stable phosphatase took place using the enzyme assays described in example 2. For example, the calcium phosphate/DNA co-precipitation method (Wigler et al., Cell 1977, vol. 16, 777–785) or the method of lipofection already described in example 3 is used for a stable transfection. The first method is described in the following. The indicated amounts refer to a 25 cm$^2$ cell-culture flask.

One day prior to the transfection the cells are uniformly disseminated in a cell density of 1–3×10$^5$/25 cm$^2$ culture surface. On the day of the transfection the culture medium is changed 4 h before the addition of the DNA precipitate. The DNA precipitate is produced as follows: 250 µl 2×HEBS buffer (280 mM NaCl, 1.5 mM Na$_2$HPO$_4$, 50 mM Hepes pH 7.1) is placed in an appropriately dimensioned container (0.5 vol 2×HEBS buffer; total volume per precipitate is 500 µl). 25 µl 2.5M CaCl$_2$ solution (final concentration 125 mM) as well as the corresponding DNA, divided according to selections DNA (500 ng), co-transfer DNA (5 µg) and carrier DNA (5 µg; sheared chromosomal DNA of the cell line used for transfection) is pipetted into another reaction container and the container filled to a total volume of 250 µl with milli-Q water. The CaCl$_2$ mixture is now added to the latter while stirring up the 2×HEBS buffer in the container. This mixture is left at room temperature for 30–60 min (formation of the precipitate) and then added into the culture medium to the cells. After an incubation time of 4–12 h, the medium is changed. The selection (medium with selection marker such as, for example, geneticin/G418™) is begun 2 days after ending the transfection.

Result

The determinations of the phosphatase activity in the non-transfixed cell lines are presented in summary fashion in table 2. According to the results, a significant amount of heat-stable phosphatase is secreted from the KB and SK-BR-3 tumor line, namely, 4.1 mU/ml and 0.5 mU/ml. A slight activity can be measured with 017 mU/ml in the culture medium of the tumor line LXFA 629L. It is known from the literature for the KB line that a dimer is synthesized from PLAP and IAP which behaves similarly to PLAP (Kodama et al., Biochem. Biophsy. Acta 1218, 163–1172, 1994) and is also quite obviously excreted. All other tumor cell lines excrete no demonstrable amounts of heat-stable phosphatase (an activity of 0.01 mU/ml is at the sensitivity boundary of the chemiluminometric test). It is shown by way of example for three tumor cell lines that after transfection of the corresponding construct pSBC SEAP/IRES/Neo$^R$ in the culture medium, heat-stable AP activity can be demonstrated. It is 4 to 20 times greater in the clone mixtures than in the non-transfected tumor cells (see table 2).

EXAMPLE 7

Orthotopic Transplantation of the Transfected Tumor Cell Line HT29 into the Intestinal Epithelium of Nude Mice An orthotopic transplantation into the caecum of nude mice in comparison to a subcutaneous implantation is shown by way of example in the following for tumor cell line HT29. The HT29 cell line used for the transplantation experiment was stably transfected for this with the SEAP-cDNA gene (vector PSBC SEAP/IRES/Neo$^R$.

Methods

Orthotopic transplantation of HT29 tumor cells into the caecum of nude mice. In order to determine the SEAP basal activity in the serum approximately 300 µl whole blood from the vena sublingualis are taken from each animal three days prior to the start of the test, the serum extracted therefrom and the SEAP activity contained is determined (see example 2). The transplantation takes place under an isoflurane/nitrous oxide inhalation anesthesia. A skin incision approximately 1 cm in length is made at the level of the sacral region with dissecting scissors and the skin generously separated from the hypodermis. The abdominal cavity is opened along the linea alba and the caecum drawn out of the abdominal cavity with iris forceps. The cells to be transplanted are resuspended and taken up in a 1 ml tuberculin syringe (1×10$^4$ cells/50 µl PBS/animal). The cell injection into the intestinal wall takes place between the caecum and the end of the ileum. The intestine is then carefully reduced, the abdominal wall sutured with catgut and the skin incision closed with Michel's clamps [suture clips]. The Michel's clamps are removed five days after the operative procedure. The withdrawals of blood take place as already described twice weekly.

Result

Figure 6A:
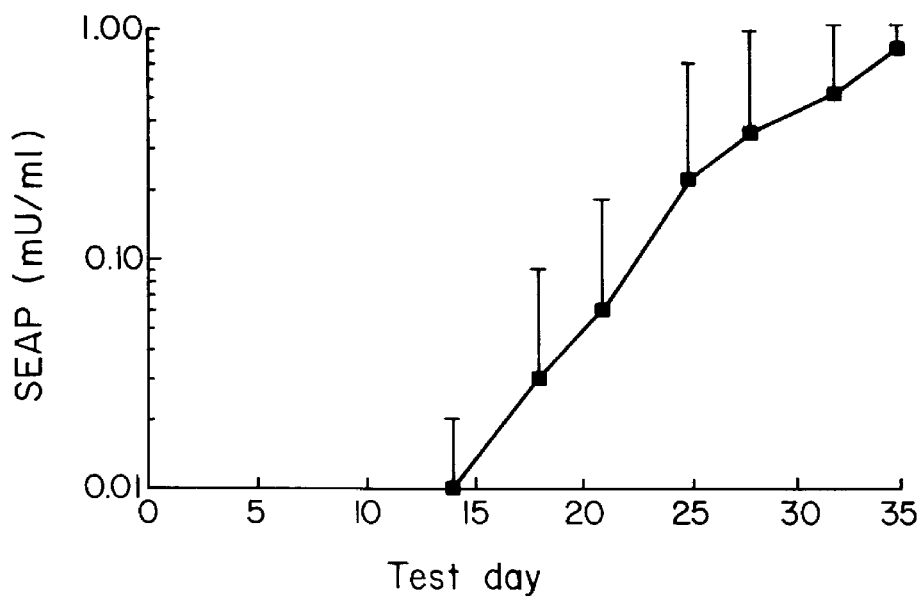
FIGS. 6A–6C show the results for the stably transfected HT29 tumor cell line.
Figure 6B:
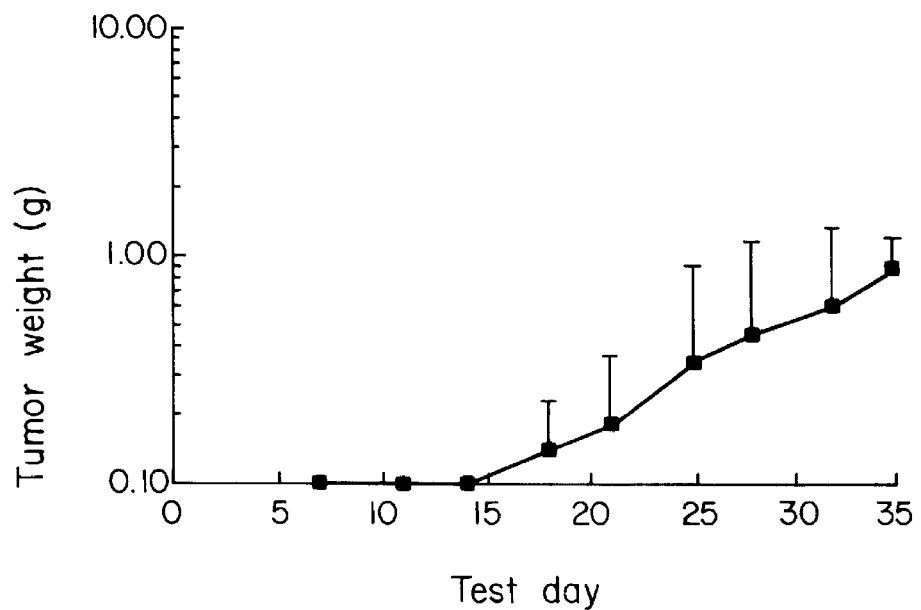
Figure 6C:
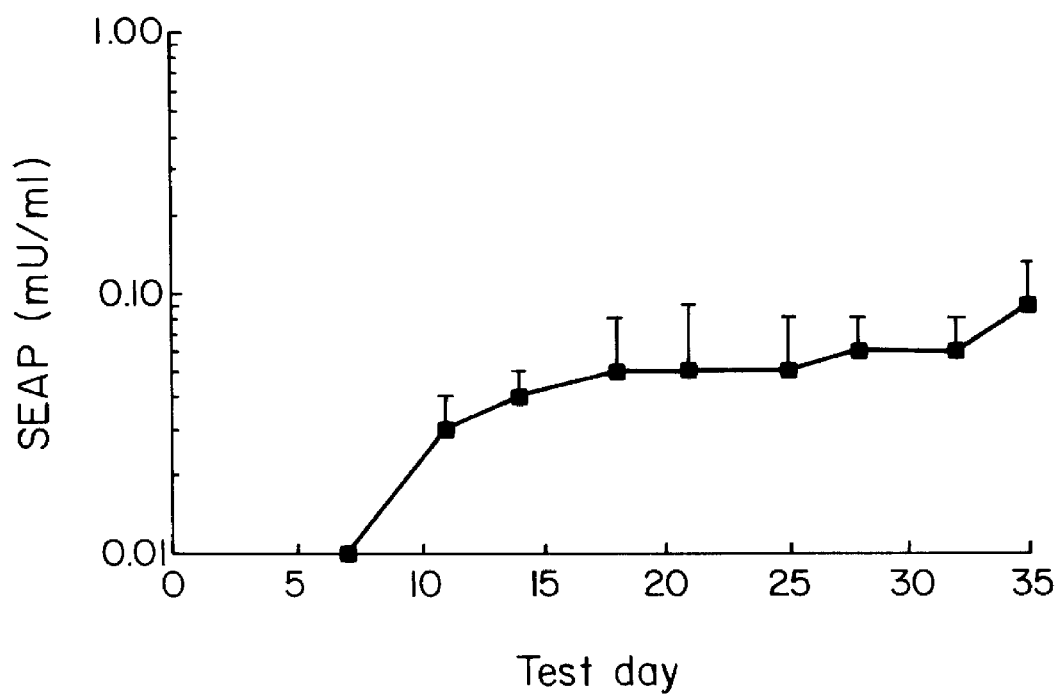

FIG. 6 shows the results for the stably transfected HT29 tumor cell line. FIGS. 6 A/B show the SEAP activity in the serum compared to the tumor mass in the case of subcutaneous transplantation in nude mice (n=6). It is clear, as in the test data previously shown already, that the vital tumor cells can be detected very sensitively via the measuring of the SEAP activity in the serum. The increase of the SEAP activity in the serum with the progression of time correlates with the tumor mass determined by palpitation. FIG. 6C shows the SEAP activities in the serum of animals with orthotopically transplanted tumors (n=4). Even if only about 10 times lower SEAP activities can be demonstrated in comparison to the test with subcutaneous transplantation, a continuous rise can be measured. This rise reflects the growth of the tumor cells in the intestinal wall, as was able to be shown after biopsy of the animals. An externally palpable tumor could not be demonstrated during the test.

References cited herein are hereby incorporated by reference.

Abbreviations

AP alkaline phosphatase
ATP adenosine-5'-phosphate
BSA bovine serum albumin
CMV cytomegalovirus
CSPD disodium3-(4-methoxyspiro{1,2-dioxetane-3,2'-(5'chloro)tricyclo-[$3.3.1.1^{3,7}$]decane}-4yl) phenylphosphate
DNA desoxyribonucleic acid
DDT dithiothreitol
EDTA ethylene diamine tetraacetate
ELISA enzyme-linked immunosorbent assay
HER human EGF-receptor like
IAP intestinal alkaline phosphatase
IRES internal ribosomal entry site
$Neo^R$ gene coding for amino glycoside-3'phosphotransferase
PBS phosphate buffered saline
PLAP human placenta-specific, alkaline phosphatase
SDS sodium docecylsulfate

TABLE 1

Summary of the various in vivo and in vitro tests with transfected NIH3T3 fibroblasts. Measuring parameters are SEAP activity in cell-culture supernatants, focus- and colony formation in vitro as transformation parameters and tumor formation in nude mice in vivo (n.d. - not determined)

| Cell line | SEAP activity (mU/ml) | Focus formation (foci/8.5 $cm^2$) | Colony formation (colonies/8.5 $cm^2$) | Tumors in nude mice | Inductor[1] |
|---|---|---|---|---|---|
| NIH3T3 | 0.01 | none | none | 0/5 | |
| NIH3T3 SEAP | 3.18 | none | none | 0/5 | |
| Mixed clone (inducible) | 0.01 | none | none | n.d. | + ← |
| NIH3T3 | 9.30 | >100 | none | 5/5 | |
| HER2/IRES/SEAP | 11.51 | >100 | none | 5/5 | + ← |
| NIH3T3 | 1.08 | 80 | none | 5/5 | |
| HER2/IRES/SEAP Mixed clone (inducible) | 0 | none | none | n.d. | + ← |
| Isolated focus | 8.72 | 85 | 80 | 5/5 | |
|  | 0.01 | none | none | n.d. | + ← |
| Individual cell | 10.16 | >100 | 72 | 5/5 | |
| clone G8[2] | 0 | none | none | 0/5[3] | + ← |
| Individual cell | 26.16 | >100 | 80 | 5/5 | |
| clone H3 | 0 | none | none | 0/5[3] | + ← |

[Note bent arrow in the inductor column - not in WP fonts.]
[1] 1 μg tetracycline or 10 ng/ml anhydrotetracycline (in vitro) and 10 mg/kg s.c. 3 × weekly (in vivo)
[2] Cells show only slight adherence in culture without tetracycline
[3] Upon injection of anhydrotetracycline on test day 0

TABLE 2

Heat-stable, alkaline phosphatase activity in culture supernatants from various tumor cell lines. Except for the cell lines AR42J and GH3 they are exclusively of human origin (n.d. - not determined)

| Tumor cell line | AP activity (mU/ml) | AP activity after stable transfection (mU/ml) |
|---|---|---|
| HT29 (ATCC HTB38) adenocarcinoma of the colon | ≈0.01 | 0.04 |
| OVXF 899L ovarian carcinoma | ≈0.01 | 0.46 |
| SK-BR-3 adenocarcinoma of the breast | 0.50 | n.d. |
| KB (ATCC CCL 17) carcinoma of the buccal mucous membrane | 4.10 | 15.57 |
| LXFA 629L adenocarcinoma of the lung | 0.17 | n.d. |
| MEXF 514L melanoma | ≈0.01 | n.d. |
| AR42J (ATCC CRL 1492) pancreatic carcinoma of the rat | 0.03 | n.d. |
| GH3 (ATCC CCL 82.1) pituitary tumor of the rat | ≈0.01 | n.d. |

SEAP secreted human placenta-specific, alkaline phosphatase
SV-40 simian virus type 40
$tetO_7$ tetracycline operator
tTA tetracycline-controlled transactivator
U units
upm revolutions per minute
VZ test time in days

What is claimed is:

1. A vector comprising a nucleotide sequence of the general formula I

R-X-A-X-IRES-X-B-X-polyA    (I)

in which

R is a regulatory nucleotide sequence for inducible gene expression, which comprises a tetracycline operator sequence and a minimal promotor, A is a gene coding for a protein which can induce a tumorigenic growth of cells, IRES is a nucleotide sequence of viral, cellular or synthetic origin which is responsible in the stage for internal initiation of translation, B is a gene coding for a detectable, secreted protein, poly(A) is a nucleotide sequence for the polyadenylation of the transcript and X is an optional linker sequence.

2. The vector according to claim 1, in which R is the nucleotide sequence tetO$_7$ CMV.

3. The vector according to claim 1, in which A is a gene coding for the receptor tyrosine kinase erbB2/HER2.

4. The vector according to claim 1, in which B is a gene coding for the secretable human placenta-specific, alkaline phosphatase.

5. A mammalian cell line stably transfected with a vector according to claim 1.

6. The mammalian cell line according to claim 5, which is a transfected NIH3T3 fibroblast.

7. A method of screening antitumor drugs comprising the steps:
   a) Construction of a vector according to one of claims 1–4,
   b) Stable transfection of a mammalian cell line with the vector obtained in step a) in the presence or absence of a compound to be tested for anti-tumor activity,
   c) Growth of the mammalian cell line obtained in step b) in a mammalian tissue,
   d) Removal of a serum from the mammalian tissue obtained in step c) and
   e) Demonstration of the reporter protein in the serum obtained in step d).

* * * * *